US005766133A

United States Patent [19]
Faisandier

[11] Patent Number: 5,766,133
[45] Date of Patent: Jun. 16, 1998

[54] CIRCUIT FOR TESTING CABLES FOR PHYSIOLOGICAL SIGNAL SENSING ELECTRODES

[75] Inventor: Yves Faisandier, Paris, France

[73] Assignee: ELA Medical S.A., Montrouge, France

[21] Appl. No.: 550,444

[22] Filed: Oct. 30, 1995

[30] Foreign Application Priority Data

Oct. 28, 1994 [FR] France .................................. 94 13008

[51] Int. Cl.$^6$ .................................................. A61B 5/0424
[52] U.S. Cl. .................................................. 600/509
[58] Field of Search ...................... 600/509; 607/63, 607/28

[56] References Cited

U.S. PATENT DOCUMENTS 5,343,870  9/1994  Gallant et al. ............... 128/711

FOREIGN PATENT DOCUMENTS

| 0 182 197 | 5/1985 | European Pat. Off. | .......... A61B 5/04 |
| 0 335 977 | 9/1988 | European Pat. Off. | .......... A61B 5/04 |
| 0 558 051 | 1/1993 | European Pat. Off. | ...... A61B 5/0424 |

*Primary Examiner*—Scott M. Getzow
*Attorney, Agent, or Firm*—Orrick, Herrington & Sutcliffe LLP

[57] ABSTRACT

A test circuit and method for the integrity of electrode cables of a typical Holter machine for the recording of physiological signals, notably cardiac activity. This machine comprises: a plurality of signal terminals (16), which are ready to be connected each to a proximal extremity (20) of a cable (18) whose distal extremity (22) is connected to an external electrode (24) to be placed on the patient; amplifiers (30) receiving signals applied on the signal terminals; and circuit means for testing the integrity of the totality of electrical connections to the patient, comprising a current source (36), means (38, 40) to apply this current on terminals and means (34) to measure the voltage drop produced by the impedance of the circuit path (42) including the cable connected to the corresponding terminal and in which circulates the test current. The test means also includes in addition a pin (54) to test an individual cable, this pin being connected to a current source and being able to be put in contact with the distal extremity (22) of a given cable (18), whose proximal extremity (20) remains connected to its terminal (16), the test current circulating (58) between this terminal and the pin. Each of a number of individual cables in a bundle of cables can thus be manually tested by the device of the present invention to discriminate defective cables from electrodes that are poorly positioned on the patient.

14 Claims, 2 Drawing Sheets

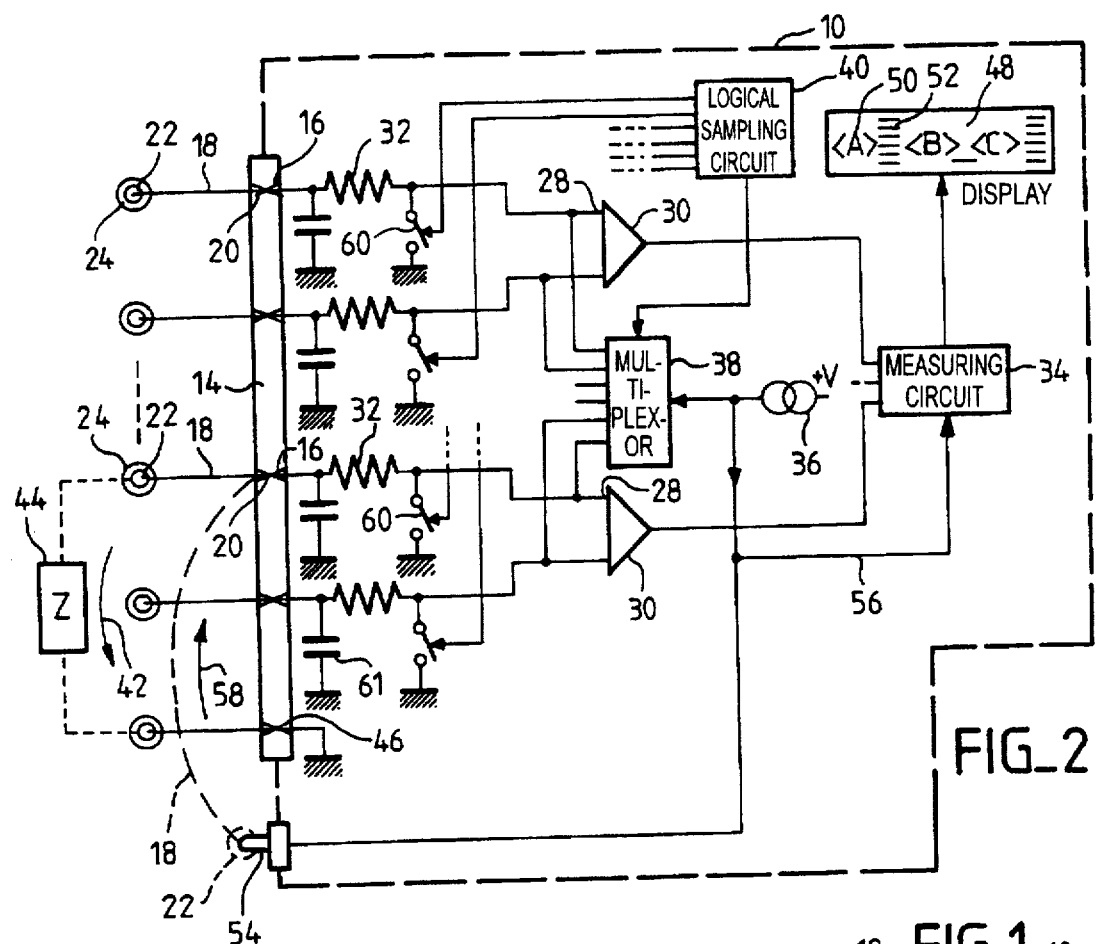
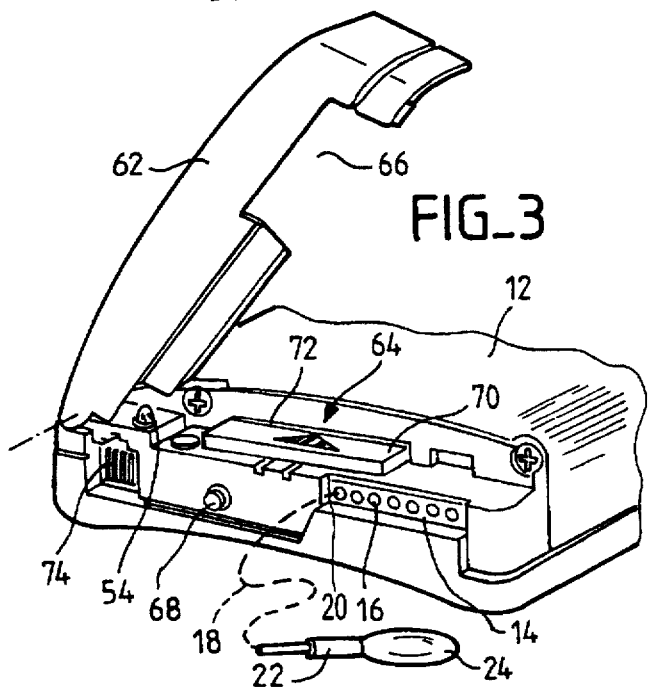
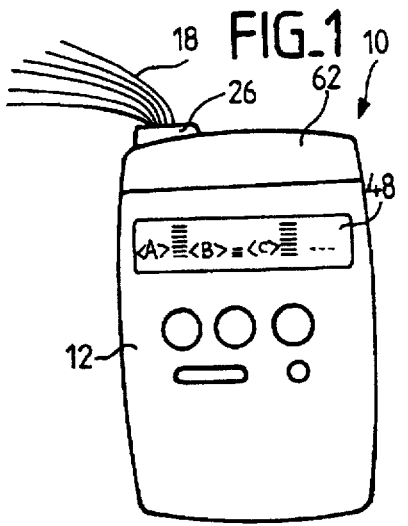
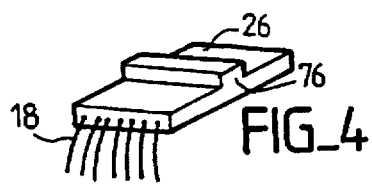

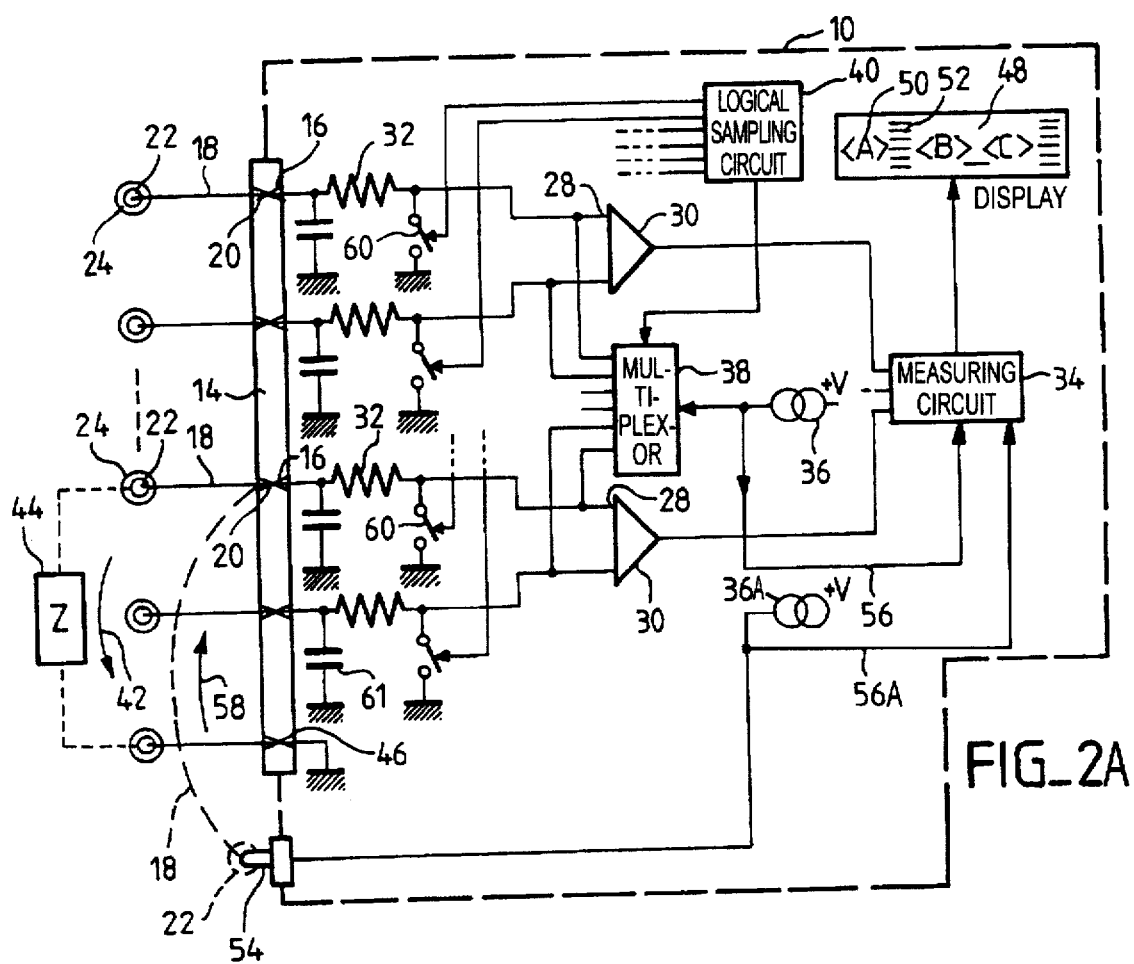
FIG_2A

CIRCUIT FOR TESTING CABLES FOR PHYSIOLOGICAL SIGNAL SENSING ELECTRODES

FIELD OF THE INVENTION

The invention concerns a typical Holter machine for recording a physiological signal, notably cardiac activity, collected by external electrodes applied on a patient.

The present invention is described with reference to "Holter" recording devices, which are ambulatory devices (carried by the patient being monitored) used to make recordings, which are obtained continuously (in an analog or digital manner) and over a long period, of cardiac activity signals (electrocardiogram) which are collected (i.e., sensed) by means of external electrodes on the patient. It should be understood however, that the present invention is not limited to this one example of recording physiological signals. Rather, the invention is equally applicable to other devices which are used for the collection or the recording of other physiological data, such as respiratory rhythms, blood pressure, etc., which devices are connected to a remote signal-acquiring electrode by the intermediary of a cable.

BACKGROUND OF THE INVENTION

The cables used to connect recording devices, such as Holter devices, to signal-acquiring electrodes, e.g., which are placed in contact with the patient, are susceptible to being cut in a manner that more or less produces an open circuit or other discontinuity. This results in a collection of signals that produces a defective recording by the machine of the physiological signals. In a system having multiple electrodes and a corresponding number of cables, to acquire the physiological signal, such as an electrocardiogram (ECG) it may be that not all of the cables are cut. Thus, some signal is acquired, but it may not be readily apparent that a defective signal is being recorded.

This aspect is particularly critical in the case of Holter recordings, to the extent that, on the one hand, the different elements of the ambulatory machine, and most notably the cables, have to be miniaturized, and are therefore rendered more fragile. On the other hand, these cables are submitted to many deformations, stress constraints, etc.

Before attaching the electrode to obtain the recording, it is therefore absolutely indispensable to insure the integrity of the cables and the good state of their connection to the recorder, on the one hand, and to the signal acquiring electrode, on the other hand.

Until the present, the integrity test has been generally realized by the use of an ohmmeter. The two extremities of the cable are connected to the ohmmeter. This requires that the cable be unplugged from the recorder after the installation of electrodes on the patient and before beginning the recording. Then, a test current is injected on each of the cables and the consequent potential difference between the two terminals corresponding, respectively, to the tested cable and to a ground electrode, is measured.

If a defect is thus detected, due to a high voltage corresponding to a high impedance, the machine emits an audible or visual message to the operator, indicative of a defect. This system of cyclic examination of all of the cables allows the operator to insure that the cables are all intact and the electrodes are correctly applied in contact with the skin, that is to say well positioned. If such is not the case, then the operator can attempt to move the electrodes until they yield a positive integrity test.

One of the problems of the cyclic testing is that it does not allow the operator to discriminate without ambiguity between a defect coming from a bad positioning of an electrode and a defect coming from a rupture of the cable, except in the case of trial and error by successive experimentation. The failure to obtain a positive integrity test, despite a repositioning of the electrode, leaves one to suppose that the anomaly comes from a physical defect of the cable and not a defective positioning of the electrode. Furthermore, there is no known device capable of performing such a discrimination.

OBJECTS AND SUMMARY OF THE INVENTION

It is, therefore, an object of the invention to remedy this disadvantage, by proposing a circuit that, in case of a negative integrity test, operates to test separately and individually the physical integrity of each cable, all the while leaving the cable connected to the recorder.

Broadly, the present invention is directed to an apparatus and method for testing the integrity of a cable having a terminal end connected to a recording device and a sensing end connected to a distal sensing electrode. One such circuit comprises:

a plurality of signal terminals, each of which is connectable to the proximal terminal end of the cable having a distal extremity (the sensing end) that is connected to a respective external electrode;

an amplifier having an input of a signal applied to said proximal terminals; and means for testing the integrity of the totality of electrical connections to the patient, these testing means comprising:

a source of test current, means for applying a test current to each of said terminal ends and means for measuring, by the amplifier, the impedance of the circuit segment including the cable connected to the corresponding terminal and in which circulates the test current.

According to a preferred embodiment of the invention, to reach the aforementioned purposes, the testing means preferably comprises a pin, this pin being connected to a current source and able to be put in contact with the distal extremity of a cable whose proximal extremity is connected to its respective signal terminal of the machine, such that the test current circulates between this signal terminal and the pin. The source of current connected to the pin can be a source of direct current or alternating current, and can in addition be the aforementioned test current source.

Preferably, the testing means comprises a means for measuring the voltage on the pin and, advantageously, means to ground the amplifier input connected to the signal terminal corresponding to the cable to be tested.

One aspect of the invention includes a machine case comprising a hinged lid that, in a closed position, blocks (i.e., covers) the pin used for testing cables so that it is inaccessible and can not be used. Advantageously, the closed position of the hinged lid also interacts with one or more of the following components of a recording device: to block the signal terminals and prevent disconnection of the cable proximal extremities from the signal terminals; to block an initialization button of the machine so that it will not inadvertently be activated to reinitialize the recorder; to lock in position an extractible support of data (i.e., a removable recording medium such as a flash memory device, floppy magnetic or optical disk and the like); and to lock in position a connector for complementary data collection coming from the patient.

BRIEF DESCRIPTION OF THE DRAWINGS

Other characteristics and advantages of the invention will appear in view of the detailed description below of a preferred embodiment of the present invention with reference to the drawings annexed in which:

FIG. 1 is a general view of a typical Holter recording machine able to be used in the present invention;

FIG. 2 is a schematic diagram of the electronic circuits of the recording machine of FIG. 1, in accordance with a preferred embodiment of the present invention;

FIG. 2A is a schematic diagram of the electronic circuits of the recording machine of FIG. 1, in accordance with an alternate embodiment of the present invention;

FIG. 3 is a partial perspective view of the posterior region of the recording machine of FIG. 1, showing various structures susceptible to be blocked by the closing down of a specific hinged lid; and FIG. 4 is an elevated three-quarters perspective view of the connector of connection of electrodes to the recording machine.

DETAILED DESCRIPTION OF THE INVENTION

Returning to FIG. 1, the recording machine 10 comprises a case 12 comprising a certain number of circuits, in themselves "state of the art", allowing the physiological signal recording and the control of the machine. These circuits do not form a part of the present invention and are known to those of ordinary skill in the art, and therefore, will not be discussed in detail.

Referring to FIG. 2, the machine 10 comprises a connector-plug 14 (as shown in the perspective view of FIG. 3) having a plurality of connector-plug signal terminals 16. In the case of a Holter recording machine for recording the ECG, there are typically seven signal terminals 16, each of which is connected to a connection cable 18 (shown in phantom in FIG. 3). The sensing end 22, the distal extremity of each cable 18, is connected to a respective external electrode 24. Electrode 24 is applied on a patient, to allow the physiological signal collection (sensing).

As illustrated in FIG. 1, the various cables 18 can be gathered in a bundle and connected to the connector-plug signal terminals 16 by the intermediary of a connector 26. Each of the signal terminals 16 is connected to an input 28 of an amplifier 30 by the intermediary of a protection resistor 32. Terminals 16 can notably, as illustrated, to be connected to amplifiers 30 configured as a differential amplifier, in a known manner.

The output of each amplifier 30 is applied to a measuring circuit 34, which performs the processing of the signals collected and amplified. The processing typically includes one or more of filtering, digitization, compression, recording, display, etc.

The machine of the present invention also includes circuit apparatus to test the integrity of cables. One such apparatus includes a source 36 of test current, a current that is injected successively and in a cyclic manner in each of cables 18 through the series resistance 32 by the intermediary of a multiplexor 38. The multiplexor 38 is controlled by a logical sampling circuit 40. The current injected in a particular cable 18 is going to circulate, if this cable is not cut (i.e., if the cable is properly conducting), followed the current path 42 across the complex impedance 44, returning to the machine by a ground terminal 46 connected to a corresponding external electrode equally applied on the patient. The intensity of the current produced by the source 36 is on the order several microamperes, e.g., from 0.1 μA when the patient is in the circuit to 10.0 μA when the cable alone is being tested. This current can be continuous (DC), alternating (AC) or, preferably, a pulsatile signal having a pulse duration on the order some tens of microseconds, to allow the stabilization of the sensing amplifiers 30 and the conversion of the signal. The circulation of the injected current produced between the concerned signal terminal 16 and ground produces a difference of potential that is proportional to the resistance of the tested cable and the ground return cable (which will be on the order of ohms, if the cables are in good condition, and megohms, if one of them is defective), increased by the impedance of the electrode-skin interference (both at the level tested and at the level of the ground return) and the internal complex impedance 44 of the body of the patient.

This voltage, amplified by the circuit 30, is all the more low given that the total impedance is itself low. In practice, the impedance is either very low or is very high according to whether or not, respectively, the tested cable and the cable ground return are in good condition and the external electrodes are well positioned.

Advantageously, the result of the successive measures is presented on the display 48 of the machine in the form of an indication 50 of the channel tested (A, B, C, ++, ...) and a bar graph 52, whose height will be all the more lower when the voltage is high. The operator of the recording device is thus informed of the quality of each of the connections. When all bars 52 of the bar graph are at their maximum height, the connection is perfect. If one or more of the bars 52 are low, the operator can attempt to move again the corresponding external electrode to see if it is possible to remedy to the defect. If all connections are defective, it concerns a defective cable connection or a defective ground return, which the system can deduce and indicate by a specific message.

As one can see it, at this first stage it is only possible to track the existence of a defect on one or several of the cable connections, but without being able to discriminate between a bad positioning of an external electrode and a physical integrity defect of the cable. As known in the prior art, the knowledge of a defect results in experimentations, namely, by trying to move again the electrode(s), or again by unplugging the bundle of cables and by testing it by means of a Ohmmeter or other continuity test device.

To overcome this difficulty, the present invention provides the machine with a circuit apparatus to test individual cables, allowing the operator to verify separately the physical integrity of a cable while leaving it connected to the signal connector 16 input of the machine 10. To this end, the machine comprises a test pin 54, for example, in form of a salient metallic element, accessible at the exterior such as illustrated in FIG. 3. This pin 54 is connected to a current source, preferably advantageously the current source 36 already used in the aforementioned stage which identified the existence of a defect. The voltage on the pin 54 is measured, for example, by a line 56 coupled to the measuring circuit 34. If a line defect has been detected in the manner indicated above, the operator proceeds then, in accordance with the present invention, to test the individual cable identified as a defective line in the first stage. To this end, the operator disconnects the distal extremity 22 from the electrode 24 and applies the extremity 22 of the cable 18 to the test pin 54. The current produced by the source 36 will, if the cable is not cut, circulate along the path 58 to the input of the signal terminal 16 of the connector-plug, through the resistance 32 and return to ground via a switch 60 controlled by the logical circuit 40 (it concerns, for example, static switches putting to ground the input of amplifiers 30 during the duration of the individual cable test phase).

One will note that the resistance 32 allows to avoid that, in case of a large overvoltage on the cable 18 (for example, due to a static electricity discharge), the switch 60 is not destroyed by the discharge and that, thereafter, a non negligible current does not flow between a point under any level of voltage of the circuit and the cable, driving to an electrolysis to the level of the electrode pasted to the patient.

In an alternate embodiment, the current source used for the individual cable test step can be a source of high frequency alternating current (typically on the order of a megahertz). In this case, capacitors 61 (pre-existing) are used to filter out radio frequency interference, and to short-circuit to ground the amplifiers inputs, thus performing the same role as switches 60. This embodiment permits eliminating the logical sampling circuit 40 that controls switches 60.

Referring to FIG. 2A, the alternate embodiment of machine 10 comprises essentially the same structure as described above in connection with FIG. 2, except that two voltage sources 36, and 36A, are illustrated. Voltage source 36A is used to energize pin 54 and is connected to measuring circuit 34 by line 56A.

Preferably, the operator (who also may be the user of the recording machine) can be guided in its manoeuver, for example, by means of a sequence of messages presented on the display 48. Thus, if the measuring circuit 34 detects a defect of a cable in the course of the first test step, it can display the message "CONNECT CABLE X" (X being the reference of the cable having the defective connection). The operator then applies the test pin 54 to the cable x. If the impedance measured is low, the message "CABLE OK" is presented on the display. By imparting to the cable movements of traction and flexion, the operator also is able to verify that the message "CABLE OK" remains well displayed during such motions. Conversely if, even by imparting to the cable movements of traction and flexion, the machine does not display the message "CABLE OK", or if this message is displayed only in an intermittent manner following the deformations applied to the cable, this indicates without ambiguity that the defect of initially detected defective cable comes from a physical integrity defect of the cable, and not from a bad positioning of the external sensing electrode on the patient.

Very advantageously, the test pin 54 can be, as illustrated in FIG. 3, built into the machine in the vicinity of various other interference elements or accessible elements of the exterior, the totality being enclosed by a common lid 62. Lid 62 is preferably hinged, with a snap-fit interconnection to the case 12. This lid 62, when it is closed, blocks the rear part 64 of the machine 10, and includes an empty space 66 allowing leave to pass the connector 26 and cables 18 connected to the connector-plug 14.

In the beginning of operation, after having had external electrodes 24 secured on the patient, the operator opens the lid 62, connects the ends 20 of cables 18 to the different signal terminals 16 of the connector-plug 14, and starts the machine by, for example, pressing an initialization button 68. The machine 10 then proceeds to perform the first step of the preliminary tracking of possible line defects, in the manner indicated above. If a defect is detected, the machine 10 then proceeds to the second step to examine one or more of the individual cables, one at a time, by means of the pin 54. This lid 62 also has for an effect to render inaccessible the test pin 54 and the initialization button 68, and equally to lock mechanically in place the connector 26, by the cut-out space 66 cooperating with a part 76 (shown in FIG. 4) of the connector 26 in an overlapping or interlocking manner, thus preventing separation of the bundle of cables from the machine 10.

Advantageously, this lid 62 can equally lock in place a static memory card 70 (notably a card of type "flash EEPROM") or any other extractible data support (magnetic or optical disk, magnetic tape, etc.) allowing the recording of data over a long duration in which will be recorded the collected signals. The card 70 is inserted in a suitable reception portion 72 in the back of the machine.

The lid 62 can equally allow to bolt mechanically not only the connector 26 of the bundle of cables connected to electrodes, but also a connector of complementary data being collected from the patient, which connector is coupled to an appropriate plug 74 situated in the machine.

The preferred embodiments illustrated and described with respect to the drawings herein are given by way of example only. In view of the above description, it will be obvious to one of ordinary skill in the art to make various modifications and changes without departing from the spirit and scope of the present invention.

I claim:

1. Apparatus for the recording of a physiological signal collected by a plurality of external electrodes applied on a patient, comprising:

a plurality of signal terminals, each signal terminal being connectable to a proximal extremity of a cable, said cable having a distal extremity connectable to one of said plurality of external electrodes;

an amplifier having an input coupled to said plurality of signal terminals; and circuit means for testing an electrical connection of each said plurality of signal terminals to the patient, said testing circuit means comprising:

a first current source having a test current output, means for selectively applying on each one of said plurality of signal terminals said test current output, and circuit means for measuring an impedance of a circuit path including a selective one signal terminal and the one of the plurality of cables connected to the selected signal terminal in response to said test current output applied to said circuit path;

wherein the apparatus further comprises:

a second current source having a second test current output; and a pin, said pin being connected to the second current source and having a contact surface able to be put in contact with the distal extremity of one of said plurality of cables whose proximal extremity is connected to the corresponding signal terminal respectively, the second test current circulating between the corresponding signal terminal, one cable, and pin.

2. The apparatus of claim 1, in which the second current source is a continuous current source.

3. The apparatus of claim 1, in which the second current source is a source of alternating current.

4. The apparatus of claim 1, in which the second current source and the first current source are the same.

5. The apparatus of claim 1, in which the circuit testing means comprises means for measuring a voltage on the pin.

6. The apparatus of claim 5, in which the circuit testing means further comprises means for grounding the input of the amplifier.

7. The apparatus of claim 1, wherein the apparatus further comprises a case of a machine, a movable lid, said lid having a closed position in which the pin is blocked and an open position in which the pin is accessible.

8. The apparatus of claim 7, in which, in said closed position, the lid blocks the plurality of signal terminals to prevent disconnection of the proximal extremities of said plurality of cables from said signal terminals.

9. The apparatus of claim 7, wherein the apparatus further comprises an initialization button and in which, in said closed position, the lid blocks the initialization button from actuation.

10. The apparatus of claim 7, wherein the apparatus further comprises an extractable data support and in which, in said closed position, the lid blocks the extractable data support from removal.

11. The apparatus of claim 7, wherein the apparatus further comprises a connector of complementary data collection coming from the patient, and in which, in said closed position, the lid locks in position said connector of complementary data.

12. In a device for recording physiological signals using a plurality of cables and external electrodes on a patient to acquire said physiological signals, each of said cables having a proximal end connector and a distal end connector, the distal end being connectable to one of the plurality of external electrodes, a test circuit for testing continuity of said cables comprising:

a plurality of signal terminals, each terminal having an input to receive one of the proximal end connectors of one of the plurality of cables and a switch circuit element operable to connect said signal terminal to a ground;

an amplifier having an input coupled to the plurality of signal terminals and an output;

a measuring circuit coupled to the amplifier output operable to measure a voltage;

a current source having a test current output;

a test pin connected to the current source;

a multiplexor having an input connected to the current source and a plurality of outputs, said plurality of outputs being connected to said plurality of signal terminals, the multiplexor being operable in a first mode to apply said test current output to each one of said plurality of cables one cable at a time, wherein said measuring circuit measures a first voltage drop across a first circuit comprising said one cable and said cable signal terminal in response to the applied test current output, and in a second mode to apply said test current to selected ones of said plurality of cables one at a time, wherein said measuring circuit measures a second voltage drop across a second circuit comprising said selected one cable, said cable signal terminal, and test pin in response to the applied test current output, said first voltage being representative of whether or not the one cable is properly connected, the second voltage being representative of the continuity of the selected one cable.

13. The apparatus of claim 12 wherein each switch circuit element further comprises a static switch, the apparatus further comprising a logic control circuit operable to operate said plurality of signal terminal switch circuit elements to apply the test current output to the one cable in each of said first and second modes.

14. The apparatus of claim 12 wherein the switch circuit element further comprises a capacitor and the current source further comprises a high frequency current source.

* * * * *